US011089981B2

(12) United States Patent
Aggarwal et al.

(10) Patent No.: US 11,089,981 B2
(45) Date of Patent: Aug. 17, 2021

(54) METHODS AND SYSTEMS FOR PERFORMING UNIVERSAL CALIBRATION TO NON-INVASIVELY DETERMINE BLOOD GLUCOSE CONCENTRATION

(71) Applicant: SAMSUNG ELECTRONICS CO., LTD., Suwon-si (KR)

(72) Inventors: Gorish Aggarwal, Karnataka (IN); Kiran Bynam, Karnataka (IN); So Young Lee, Daejeon (KR); Ibrahim A, Karnataka (IN); Sujit Jos, Karnataka (IN); Rahul Arora, Karnataka (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 239 days.

(21) Appl. No.: 16/459,785

(22) Filed: Jul. 2, 2019

(65) Prior Publication Data

US 2020/0022627 A1 Jan. 23, 2020

(30) Foreign Application Priority Data

Jul. 23, 2018 (IN) .............................. 201841027614
Mar. 25, 2019 (KR) ........................ 10-2019-0033931

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/0075* (2013.01); *A61B 5/1495* (2013.01);
(Continued)

(58) Field of Classification Search
CPC ..... A61B 5/14532; A61B 5/1455; A61B 5/72; A61B 5/7221; A61B 5/7225; A61B 5/725; A61B 5/7246; A61B 5/7264

See application file for complete search history.

(56) References Cited

U.S. PATENT DOCUMENTS 5,267,152 A   11/1993 Yang et al.
6,968,221 B2  11/2005 Rosenthal
(Continued)

OTHER PUBLICATIONS

Liu et al., "Next step of non-invasive glucose monitor by NIR technique from the well controlled measuring condition and results", Optical and Quantum Electronics, 2005, p. 1305-1317, 14 pages total.

*Primary Examiner* — Eric F Winakur
(74) *Attorney, Agent, or Firm* — Sughrue Mion, PLLC (57) ABSTRACT

A method includes processing near infrared spectroscopy (NIR) spectra and pure spectra, to obtain a preprocessed NIR spectra, wherein the preprocessed NIR spectra includes any one or any combination of a training data of a plurality of subjects, a calibration data of a test subject and a validation data of the test subject, extracting a dominant feature set from the preprocessed NIR spectra, wherein the dominant feature set includes at least one preprocessed NIR spectrum corresponding to each of the training data, the calibration data and the validation data, and determining a blood glucose concentration of the test subject, using the training data of the plurality of subjects and based on the extracted dominant feature set.

18 Claims, 8 Drawing Sheets
(4 of 8 Drawing Sheet(s) Filed in Color)

(51) Int. Cl.
    *A61B 5/00*      (2006.01)
    *G06N 20/20*     (2019.01)
    *A61B 5/1495*    (2006.01)

(52) U.S. Cl.
    CPC ............ *G06N 20/20* (2019.01); *A61B 5/1455* (2013.01); *A61B 5/7246* (2013.01); *A61B 2560/0223* (2013.01); *A61B 2562/0238* (2013.01)

(56) References Cited

U.S. PATENT DOCUMENTS

| | | |
|---|---|---|
| 7,039,446 B2 | 5/2006 | Ruchti et al. |
| 7,830,519 B2 | 11/2010 | Mah et al. |
| 7,952,692 B2 | 5/2011 | Primack et al. |
| 8,275,433 B2 | 9/2012 | Yamakoshi |
| 9,448,164 B2 | 9/2016 | Gulati et al. |
| 9,662,047 B2 | 5/2017 | Barman et al. |
| 2005/0119541 A1* | 6/2005 | Lorenz .............. A61B 5/14532 600/316 |
| 2006/0063983 A1 | 3/2006 | Yamakoshi |
| 2006/0167350 A1* | 7/2006 | Monfre .............. A61B 5/7264 600/322 |
| 2010/0324398 A1* | 12/2010 | Tzyy-Ping ......... A61B 5/14532 600/365 |
| 2015/0369725 A1 | 12/2015 | Carvalho Sousa et al. |
| 2017/0055891 A1 | 3/2017 | Chaychi |

\* cited by examiner

METHODS AND SYSTEMS FOR PERFORMING UNIVERSAL CALIBRATION TO NON-INVASIVELY DETERMINE BLOOD GLUCOSE CONCENTRATION

CROSS-REFERENCE TO RELATED APPLICATIONS

This application claims priority from Indian Application No. 201841027614, filed on Jul. 23, 2018, in the Indian Patent Office, and Korean Patent Application No. 10-2019-0033931, filed on Mar. 25, 2019, in the Korean Intellectual Property Office, the disclosures of which are incorporated herein by reference in their entireties.

BACKGROUND

1. Field

Methods and apparatuses consistent with example embodiments relate to monitoring blood glucose concentration, and more particularly, to performing universal calibration to non-invasively determine blood glucose concentration.

2. Description of the Related Art

Continuous Glucose monitoring (CGM) is used for testing level of blood glucose concentration in a subject at regular intervals. CGM can be performed either invasively or non-invasively. In an invasive method, the skin of a subject is pierced to obtain a blood sample for testing.

However, non-invasive methods do not require any collection of blood sample for finding glucose concentration. Some of the methods used for non-invasive glucose monitoring are Mid Infrared (Mid IR), Near Infrared (NIR), and Raman spectroscopy. In recent years, NIR method is commonly used for continuous glucose monitoring, in which the IR waves are made to pass through the skin and absorption of the IR waves by the subcutaneous portion of skin helps in determining the glucose level.

The absorption of a wave by any sample is defined by the Beer Lambert law as:

$$A = \log\left(\frac{I}{I_0}\right) = \epsilon C d \quad (1)$$

Where $\epsilon$ is the absorptivity coefficient, C is the concentration of component in sample and d is penetration depth.

If a sample is composed of different constituents, then its overall absorbance can be given as $$A = \epsilon_1 C_1 d + \epsilon_2 C_2 d + \ldots + \epsilon_n C_n d \quad (2)$$

The NIR absorption spectra of the skin is composed of absorption of several components such as water, fat, protein (Collagen and keratin), amino acids and glucose. Therefore, $$A_{NIR} = A_{water} + A_{Fat} + A_{Collagen} + A_{Keratin} + A_{Acid} + A_{Glucose} \quad (3)$$

Monitoring of blood glucose concentration non-invasively is very challenging as the concentration of glucose in blood is several orders lesser than that of other constituents. The glucose information can be buried under the noise and drift components of the NIR spectra. Approximate orders of concentration of different constituents are shown in the below table:

| Constituent | Water | Fat | Protein | Elastin/Acid | Glucose |
|---|---|---|---|---|---|
| Order of concentration (~) | $10^0$ | $10^{-1}$ | $10^{-3}$ | $10^{-3}$ | $10^{-4}$ |

The existing blood glucose prediction mechanisms address measurement of blood glucose using only specific Infrared spectroscopy (IR) containing water absorption peaks and uses transmitted Electromagnetic radiation (EM) radiation from skin to measurement region, such as blood vessels. Further, collected light/EM is analyzed and compared against a stored reference calibration curve to calculate the blood glucose. However, the existing glucose determining mechanisms assume that the background interference is common for all ranges of the near-infrared region. These methods use a reference calibration curve, which varies from subject to subject and hence universality is not guaranteed.

Another existing glucose determining mechanism measures constituents of the blood through NIR spectroscopy. It uses a spectrum subtraction generator to generate a plurality of spectrum subtractions from the spectra measured by spectrum analyzer at different times. A multi regression model is used based on Partial Least Squares Regression (PLS) or Principal Component Regression (PCR). However, the existing glucose determining mechanisms do not distinguish between different blood components such as glucose/fat/lipid, and so on.

Another existing glucose determining mechanism uses an NIR spectroscopy technique and uses Monte Carlo simulation to remove noise in single subject data. This method achieves good results for same day validation but performs poorly for different day validation.

SUMMARY

According to embodiments, there is provided a method of determining a blood glucose concentration, using near infrared spectroscopy (NIR) spectra that is measured by an electronic device that includes at least one processor, the method including processing, by the at least one processor, the NIR spectra and pure spectra, to obtain a preprocessed NIR spectra, wherein the preprocessed NIR spectra includes any one or any combination of a training data of a plurality of subjects, a calibration data of a test subject and a validation data of the test subject. The method further includes extracting, by the at least one processor, a dominant feature set from the preprocessed NIR spectra, wherein the dominant feature set includes at least one preprocessed NIR spectrum corresponding to each of the training data, the calibration data and the validation data, and obtaining, by the at least one processor, a plurality of homogenized feature sets of the validation data, wherein each of the plurality of homogenized feature sets is homogenized with respect to the extracted dominant feature set in the training data of one of the plurality of subjects and the extracted dominant feature set in the calibration data of the test subject. The method further includes determining, by the at least one processor, the blood glucose concentration of the test subject, using the training data of the plurality of subjects and the plurality of homogenized feature sets of the validation data.

The processing of the NIR spectra and the pure spectra may include filtering, by the at least one processor, the NIR spectra to remove unwanted components in a frequency domain, from the NIR spectra, obtaining, by the at least one processor, orthogonal pure spectra by applying transformations on the pure spectra, removing, by the at least one processor, components other than glucose and water, from the filtered NIR spectra, using the orthogonal pure spectra, and removing, by the at least one processor, a drift from a time domain of the NIR spectra from which the components are removed.

The filtering of the NIR spectra may include filtering, by the at least one processor, noise from the NIR spectra, using a Savitzky-Golay filter, and removing, by the at least one processor, a linear drift from a wavelength domain of the NIR spectra from which the noise is filtered, by differentiating the NIR spectra with respect to wavelength.

The extracting of the dominant feature set may include computing, by the at least one processor, correlations between a glucose concentration of the training data and each of the preprocessed NIR spectra in the training data, and choosing, by the at least one processor, the dominant feature set, based on a maximum of the computed correlations.

The obtaining of the plurality of homogenized feature sets may include obtaining, by the at least one processor, a singular homogenized feature set of the validation data, wherein the singular homogenized feature set is homogenized with respect to the extracted dominant feature set of the training data of the one of the plurality of subjects and the calibration data, and repeating, by the at least one processor, the obtaining of the singular homogenized feature set, to obtain the plurality of homogenized feature sets of the validation data.

The obtaining of the singular homogenized feature set may include obtaining, by the at least one processor, a linear approximation relation for each of features in the extracted dominant feature set with respect to corresponding glucose concentrations of the training data and the calibration data, computing, by the at least one processor, an adjustment factor for each of the features in the extracted dominant feature set for the calibration data, keeping the training data as a reference, based on the linear approximation relation, and mapping, by the at least one processor, each of the features in the extracted dominant feature set of the validation data by subtracting each of the features in the extracted dominant feature set of the validation data respectively from the computed adjustment factor for each of the features, to obtain the singular homogenized feature set of the validation data.

The computing of the adjustment factor for each of the features in the extracted dominant feature set of the calibration data may include calculating, by the at least one processor, a mean glucose value for the training data, computing, by the at least one processor, NIR feature values for each of the features in the extracted dominant feature set of the training data and the calibration data at the calculated mean glucose value, using the linear approximation relation, and subtracting, by the at least one processor, the computed NIR feature values of the calibration data from the computed NIR feature values of the training data, to obtain the adjustment factor for each of the features in the extracted dominant feature set.

The determining of the blood glucose concentration may include training, by the at least one processor, an ensemble of regression models separately with the extracted dominant feature set in the training data of the one of the plurality of subjects, computing, by the at least one processor, a plurality of regression outputs from the trained ensemble of regression models, taking an input for each of the ensemble of regression models respectively as the plurality of homogenized feature sets of the validation data, estimating, by the at least one processor, a plurality of weights of a meta-classifier for each of the ensemble of regression models, using the training data of the plurality of subjects, and determining, by the at least one processor, the blood glucose concentration of the test subject by weighted averaging of the computed plurality of regression outputs, based on the estimated plurality of weights of the meta-classifier.

The estimating of the plurality of weights may include computing, by the at least one processor, a plurality of model outputs from the ensemble of regression models, taking the input for each of the ensemble of regression models as a complete set of the training data of the plurality of subjects, calculating, by the at least one processor, a plurality of model correlations by computing correlation between the computed plurality of model outputs and glucose concentrations of the training data of the plurality of subjects, and scaling, by the at least one processor, the calculated plurality of model correlations, to obtain the plurality of weights of the meta-classifier for each of the ensemble of regression models.

According to embodiments, there is provided an electronic device for determining a blood glucose concentration, using near infrared spectroscopy (NIR) spectra, the electronic device including at least one processor implementing a pre-processing unit configured to process the NIR spectra and pure spectra, to obtain a preprocessed NIR spectra, wherein the preprocessed NIR spectra includes any one or any combination of a training data of a plurality of subjects, a calibration data of a test subject and a validation data of the test subject. The electronic device further includes a feature set extraction unit configured to extract a dominant feature set from the preprocessed NIR spectra, wherein the dominant feature set includes at least one preprocessed NIR spectrum corresponding to each of the training data, the calibration data and the validation data, and a feature homogenization unit configured to obtain a plurality of homogenized feature sets of the validation data, wherein each of the plurality of homogenized feature sets is homogenized with respect to the extracted dominant feature set in the training data of one of the plurality of subjects and the extracted dominant feature set in the calibration data of the test subject. The electronic device further includes an ensemble learning unit configured to determine the blood glucose concentration of the test subject, using the training data of the plurality of subjects and the plurality of homogenized feature sets of the validation data.

The pre-processing unit may include a frequency domain filtering unit configured to filter the NIR spectra to remove unwanted components in a frequency domain, a data whitening unit configured to obtain orthogonal pure spectra by applying transformations on the pure spectra, an extended multiplicative scatter correction (EMSC) unit configured to remove components other than glucose and water, from the filtered NIR spectra using the orthogonal pure spectra, and a drift removal unit configured to remove a drift from a time domain of the NIR spectra from which the components are removed.

The frequency domain filtering unit may be further configured to filter noise from the NIR spectra, using a Savitzky-Golay filter, and remove a linear drift from a wavelength domain of the NIR spectra from which the noise is filtered, by differentiating the NIR spectra with respect to wavelength.

The feature set extraction unit may be further configured to compute correlations between a glucose concentration of the training data and each of the preprocessed NIR spectra in the training data, and choose the dominant feature set, based on a maximum of the computed correlations.

The feature homogenization unit may be further configured to obtain a singular homogenized feature set of the validation data, wherein the singular homogenized feature set is homogenized with respect to the extracted dominant feature set of the training data of the one of the plurality of subjects and the calibration data, and repeat the obtaining the singular homogenized feature set, to obtain the plurality of homogenized feature sets of the validation data.

The feature homogenization unit may be further configured to obtain a linear approximation relation for each of features in the extracted dominant feature set with respect to corresponding glucose concentrations of the training data and the calibration data, compute an adjustment factor for each of the features in the extracted dominant feature set for the calibration data, keeping the training data as a reference, based on the linear approximation relation, and map each of the features in the extracted dominant feature set of the validation data by subtracting each of the features in the extracted dominant feature set of the validation data respectively from the computed adjustment factor for each of the features, to obtain the singular homogenized feature set of the validation data.

The feature homogenization unit may be further configured to calculate a mean glucose value for the training data, compute NIR feature values for each of the features in the extracted dominant feature set of the training data and the calibration data at the calculated mean glucose value, using the linear approximation relation, and subtract the computed NIR feature values of the calibration data from the computed NIR feature values of the training data to, obtain the adjustment factor for each of the features in the extracted dominant feature set.

The ensemble learning unit may be further configured to train an ensemble of regression models separately with the extracted dominant feature set in the training data of the one of the plurality of subjects, compute a plurality of regression outputs from the trained ensemble of regression models, taking an input for each of the ensemble of regression models respectively as the plurality of homogenized feature sets of the validation data, estimate a plurality of weights of a meta-classifier for each of the ensemble of regression models, using the training data of the plurality of subjects, and determine the blood glucose concentration of the test subject by weighted averaging of the computed plurality of regression outputs, based on the estimated plurality of weights of the meta-classifier.

The ensemble learning unit may be further configured to compute a plurality of model outputs from the ensemble of regression models, taking the input for each of the ensemble of regression models as a complete set of the training data of the plurality of subjects, calculate a plurality of model correlations by computing correlation between the computed plurality of model outputs and glucose concentrations of the training data of the plurality of subjects, and scale the calculated plurality of model correlations, to obtain the plurality of weights of the meta-classifier for each of the ensemble of regression models.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Example embodiments herein, the various features, and advantageous details thereof are explained more fully with reference to the non-limiting embodiments that are illustrated in the accompanying drawings and detailed in the following description. Descriptions of well-known components and processing techniques are omitted to not unnecessarily obscure the embodiments herein. The description herein is intended to facilitate an understanding of ways in which the example embodiments herein can be practiced and to further enable those of skill in the art to practice the example embodiments herein. Accordingly, this disclosure may not be construed as limiting the scope of the example embodiments herein.

The embodiments herein describe methods and systems for performing universal calibration to non-invasively determine blood glucose concentration.

In detail, a method includes processing a NIR spectra and pure spectra to obtain a preprocessed NIR spectra, wherein the NIR spectra includes any one or any combination of a training data of a plurality of subjects, a calibration data of a test subject and a validation data of the test subject, extracting a dominant feature set from the preprocessed NIR spectra, obtaining a plurality of homogenized feature sets of the validation data, and determining the blood glucose concentration of the test subject, using the training data of a plurality of subjects and correspondingly, the homogenized feature sets of the validation data.

Referring now to the drawings, and more particularly, to FIGS. 1 through 7, in which similar reference characters denote corresponding features consistently throughout the figures, there are shown example embodiments.

The term 'subject' as used herein can be any living creature or a part of a living creature, such as, but not limited to, a human being, an animal, a bird, aquatic creatures, and so on, whose body contains blood.

Figure 1:
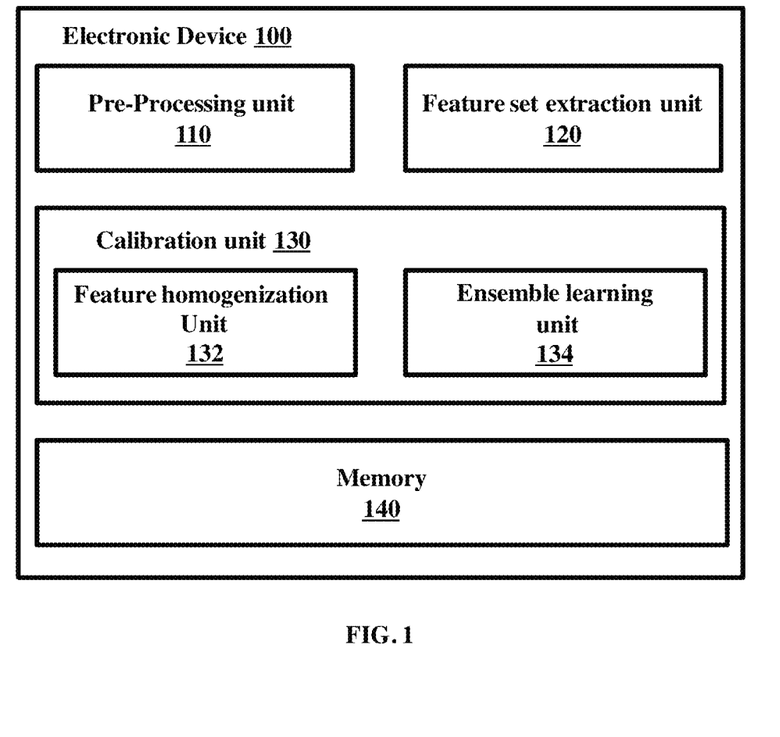
FIG. 1 is a block diagram illustrating an electronic device for calibrating and predicating blood glucose concentrations, according to embodiments.

FIG. 1 is a block diagram illustrating an electronic device 100 for calibrating and predicating blood glucose concentrations, according to embodiments. The electronic device 100 can be any one or any combination of, but not restricted to, a mobile phone, a smartphone, a tablet, a phablet, a personal digital assistant (PDA), a wearable computing device, an Internet of Things (IoT) device, a glucose monitoring device, a glucometer or any other electronic device.

The embodiments herein provide a method and electronic device 100 for performing universal calibration to non-invasively determine blood glucose concentration of a test subject. The electronic device 100 includes at least one processor implementing a pre-processing unit 110, a feature set extraction unit 120, a calibration unit 130 and a memory 140. Further, the calibration unit 130 includes a feature homogenization unit 132 and an ensemble learning unit 134. The pre-processing unit 110 can be configured to process NIR spectra, wherein the NIR spectra includes any one or any combination of a training data of a plurality of subjects, a calibration data of the test subject and a validation data of the test subject. In embodiments, the NIR spectra and pure spectra is processed to obtain a preprocessed NIR spectra by removing a noise component, a time variant drift component, a frequency variant drift component and other components present in the NIR spectra. The feature set extraction unit 120 can be configured to extract a dominant feature set from the preprocessed NIR spectra, wherein this dominant feature set includes at least one preprocessed NIR spectrum corresponding to each of the training data, the calibration data and the validation data.

The pre-processing unit 110 has not removed any of the wavelengths or any of the time samples present in the NIR spectra. In an example, the pre-processing unit 110 has filtered the time samples so the preprocessed NIR spectra include 129 time samples, wherein there are 129 wavelengths present in the NIR spectra. Each of the wavelengths can be considered as a feature, and so the NIR spectra will have 129 features.

Further, the feature homogenization unit 132 can obtain a plurality of homogenized feature sets of the validation data, wherein each feature set is homogenized with respect to the dominant feature set in the training data of a distinct subject and the dominant feature set in the calibration data of the test subject. In embodiments, the method of obtaining the plurality of homogenized feature sets for the validation data includes obtaining a singular homogenized feature set of the validation data homogenized with respect to the dominant feature set of the training data of the singular subject and the calibration data. Further, the method includes repeating the above step to obtain the plurality of homogenized feature set for the validation data.

Further, the ensemble learning unit 134 can determine a blood glucose concentration of the test subject by training an ensemble of regression models each trained separately with the dominant feature set in the training data of a distinct subject. Further, the method includes computing a plurality of regression outputs from the ensemble of regression models taking the input for each of the regression models as the corresponding homogenized feature set of the validation data. Further, the method includes estimating a plurality of weights of a meta-classifier for each of the regression models using the training data of a plurality of subjects. Further, the method includes determining the blood glucose concentration of the test subject by weighted averaging of the plurality of regression outputs based on the weights of the meta-classifier.

The memory 140 can be configured to store the training data, the pure spectra, the calibration data, validation data and the determined glucose concentration of the test subject. The memory 140 may include one or more non-transitory computer-readable storage media. The memory 140 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 140 may, in some examples, be considered a non-transitory storage medium. The term "non-transitory" may indicate that the storage medium is not embodied in a carrier wave or a propagated signal. However, the term "non-transitory" may not be interpreted to mean that the memory 140 is non-movable. In some examples, the memory 140 can be configured to store larger amounts of information than the memory. In examples, a non-transitory storage medium may store data that can, over time, change (e.g., in Random Access Memory (RAM) or cache). The memory 140 may further store instructions, and the at least one processor may be configured to execute the stored instructions to cause the at least one processor to perform the functions of the pre-processing unit 110, the feature set extraction unit 120, and the calibration unit 130.

FIG. 1 shows example units of the electronic device 100, but it is to be understood that other embodiments are not limited thereon. In other embodiments, electronic device 100 may include less or more number of units. Further, the labels or names of the units are used only for illustrative purpose and does not limit the scope of the embodiments. One or more units can be combined together to perform same or substantially similar function in the electronic device 100.

Figure 2A:
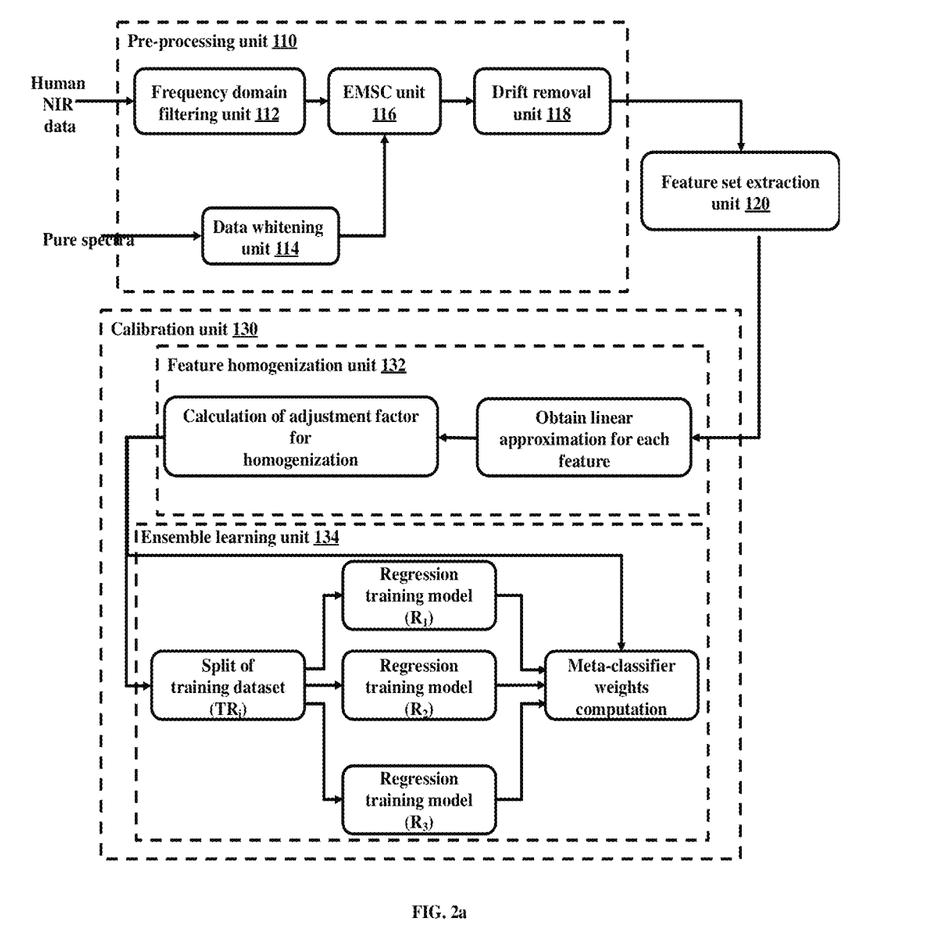
FIG. 2a is a block diagram illustrating flow of training and calibration data for calibrating and predicating blood glucose concentrations, according to embodiments.
Figure 2B:
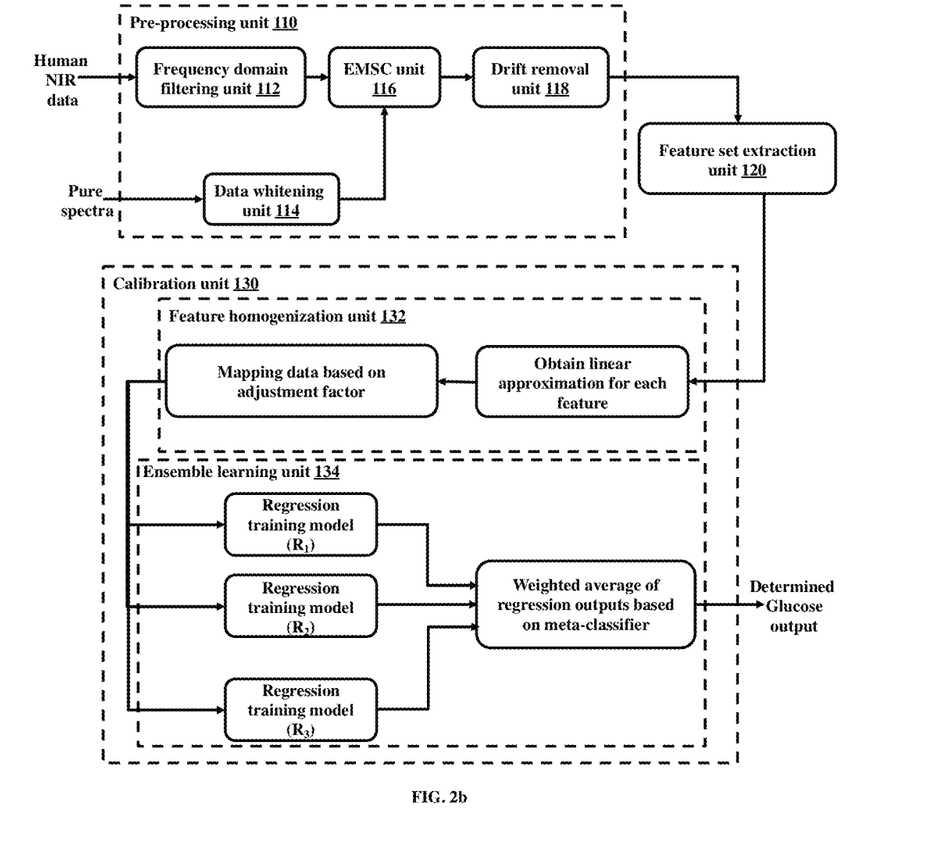
FIG. 2b is a block diagram illustrating flow of validation data for predicating blood glucose concentrations, according to embodiments.

FIG. 2a is a block diagram illustrating flow of training and calibration data for calibrating and predicating blood glucose concentrations, according to embodiments. FIG. 2b is a block diagram illustrating flow of validation data for predicating blood glucose concentrations, according to embodiments. The embodiments herein provide the electronic device 100 for performing universal calibration to non-invasively determine blood glucose concentration. The electronic device 100 includes the pre-processing unit 110; the feature set extraction unit 120 and the calibration unit 130. Further, the pre-processing unit 110 includes a frequency domain filtering unit 112, a data whitening unit 114, an Improved Extended Multiplicative Scatter Correction (EMSC) unit 116, and a drift removal unit 118. Further, the calibration unit 130 includes the feature homogenization unit 132 and the ensemble learning unit 134.

The pre-processing unit 110 can be configured to receive NIR spectra from a plurality of subjects. The NIR spectra includes any one or any combination of a training data of a plurality of subjects, a calibration data of the test subject and a validation data of the test subject.

The frequency domain filtering unit 112 can be configured to remove the unwanted components in the frequency domain such as noise and frequency variant drift component. A Savitzky-Golay (SG) filter present in the frequency domain filtering unit 112 filters the noise present in the NIR spectra. The differentiation of the NIR spectra with respect to wavelength removes a linear drift present in the wavelength domain of the NIR spectra. The data whitening unit 114 can be configured to obtain orthogonal pure spectra after applying transformations on the pure spectra. The data whitening unit 114 includes mean and standard deviation normalization of the pure spectra, calculate eigen vectors of the normalized pure spectra and apply the whitening transformation, to obtain the orthogonal pure spectra. Assuming the pure spectra to be X and the normalized pure spectra to be $\bar{X}$ the eigen vectors E and D can be calculated using:

$$[E,D]=\text{eig}(\tilde{X}'^*\tilde{X}) \quad (4)$$

The whitening transformation to obtain the orthogonal pure spectra $\tilde{X}$, can be given as:

$$\tilde{X}=ED^{-1/2}E'\tilde{X} \quad (5)$$

Further, data whitening will make the covariance matrix of data whitened NIR spectra $R_{xx}$ equal to $I_n$:

$$R_{xx}=E(\tilde{X}'^*\tilde{X})=I_n \quad (6)$$

This helps to ensure that data whitened NIR spectra X is orthogonal and their projections over each other are zero.

Once the noise and the drift have been removed from the NIR spectra and the pure spectra made orthogonal, the NIR spectra and the orthogonal pure spectra is further given to the EMSC unit 116. The EMSC unit 116 can be configured to remove components other than glucose and water present in the NIR spectra using the orthogonal pure spectra. The EMSC unit 116 applies extended multiplicative scatter correction (EMSC) method on the NIR spectra, uses the orthogonal pure spectra and regress for their compositions in the NIR spectra. For instance, let Y be any NIR spectra including of various pure spectra $X_1, X_2, \ldots, X_k$ for different blood components. Then, Y can be resolved using linear regression at any given wavelength as follows:

$$Y(n)=a_0+\Sigma_{k=1}^M a_k X_k \quad (7)$$

Where $a_k$ are the strengths of blood component and $a_0$ is the DC component.

Considering $X_1$ as the Glucose spectra, it can be obtained by subtracting other components in the given spectra:

$$X_1=Y-a_0-\Sigma_{k=2}^M a_k X_k \quad (8)$$

The other components include such as, but not limited to, absorption water, absorption fat and absorption collagen, absorption keratin, absorption acid or the like.

Now, the NIR spectra may include only the glucose component and the drift component in time domain. The drift removal unit 118 can be configured to remove the drift present in the time domain of the NIR spectra. Now, the NIR spectra may contain only the glucose component, and thus, the NIR spectra can now be given to the feature set extraction unit 120.

The feature set extraction unit 120 can be configured to extract a dominant feature set from the preprocessed NIR spectra, wherein this dominant feature set includes at least one preprocessed NIR spectrum corresponding to each of the training data, the calibration data and the validation data. The output of the pre-processing unit 110 is the preprocessed NIR spectra, which includes the NIR spectra at a pre-defined number of wavelengths (in the example herein, the number of wavelengths is 129). The pre-processing unit 110 retains the 129 wavelengths at each time, samples captured in the NIR spectra. As each of the wavelengths can be considered as a feature, the processed NIR spectra has features equal to the number of wavelengths. For example, the wavelength of the NIR spectra range from 1000 to 2400 nm. Let's say one of the features can be a spectrum captured at 1200 nm. The dominant feature set extracted by the feature set extraction unit 120 will pick a few features from the total number of wavelengths (in the example herein, 129). These features are picked on the basis of the correlations computed between the glucose concentration of the training data and each of these features in the training data. These features/wavelengths, which form the dominant feature set, shall remain common for the training data, the calibration data, and the validation data.

Further, the feature set extraction unit 120 can be configured to split the NIR data into two sets, one is the training data and the calibration data and the other one is the validation data. Further, the training data and calibration data can be given to the feature homogenization unit 132. The feature homogenization unit 132 can be configured to computing correlations between the glucose concentration of the training data and each of the preprocessed NIR spectrum in the training data. Further, the feature homogenization unit 132 can be configured to repeating the above step to obtain the plurality of homogenized feature set for the validation data. The step to obtain the singular homogenized feature set of the validation data in the feature homogenization unit 132 can be configured to obtain a linear approximation relation for each feature in the dominant feature set with respect to the corresponding glucose concentrations of the training data and the calibration data. Further, this step can be configured to for homogenization, calculate an adjustment factor for each feature in the dominant feature set for the calibration data keeping the training data as reference. Further, this step can be configured to map each feature in the dominant feature set of the validation data by the subtracting it from the corresponding adjustment factors to obtain the singular homogenized feature set of the validation data.

Further, the dominant feature set in the training data can be split into different subsets based on the individual subject training data using the ensemble learning unit 134 to train an ensemble of regression models. The spilt can be done based on the individual subject training. For example, the entire data includes the NIR spectra and its corresponding glucose concentrations of subject 1, subject 2, subject 3, and subject 4. Subject 1, subject 2, and subject 3 can provide the training data and subject 4 can be the test subject. Thus, the NIR spectra and the corresponding glucose concentrations of subject 1, subject 2, and subject 3 can be the training data. The calibration data will be composed of the initial few time samples of the NIR spectra (~4-5 may be enough) of the test subject (in the example herein, subject 4) and the corresponding glucose concentrations. The validation data will then be composed of the remaining time samples of the NIR spectra of the test subject (in the example herein, subject 4) and the corresponding glucose concentrations.

The split of training data used to train the ensemble of regression models can be based on different data for each subject contributing to the training data (in the example herein, subject 1-subject 2-subject 3) as shown in FIG. 2a. It may be noted the homogenization of the validation data in the feature homogenization unit 132 was done multiple times based on the split of training data (in the example herein, 3). This can lead to generation of the plurality of homogenized feature sets each keeping a separate training data split as reference. In the example herein, the data of subject 4 shall be homogenized separately with respect to the data of subject 1, subject 2 and subject 3. These plurality of homogenized feature sets of the validation data can be used as an input to the correspondingly trained regression model to compute a plurality of regression output as shown in FIG. 2b. As shown in FIG. 2a and FIG. 2b, the feature set extraction unit 120, the path is same for the training data, calibration data and the validation data.

Figure 3:
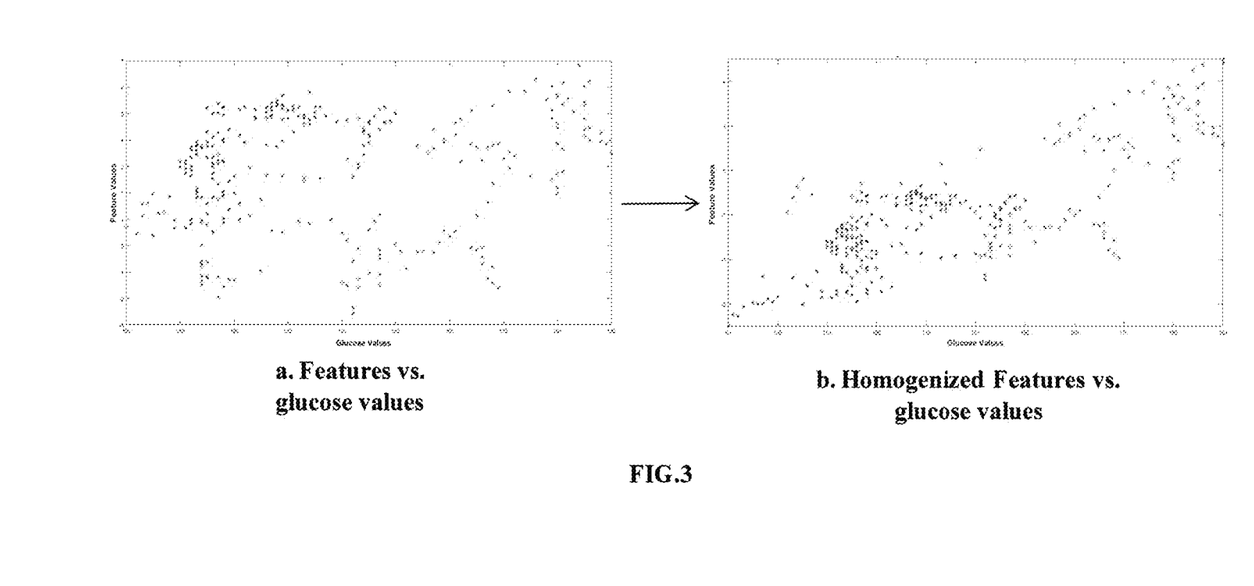
FIG. 3 is diagram of plots representing feature homogenization of validation data keeping training data as a reference, according to embodiments.

FIG. 3 is a diagram of plots representing feature homogenization of validation data keeping training data as a reference, according to embodiments. The feature homogenization unit 132 can be configured to obtain a plurality of homogenized feature sets of the validation data each homogenized with respect to the dominant feature set in the training data of a distinct subject and the dominant feature set in the calibration data of the test subject. For example, for any feature in the dominant feature set of the training data $Y_{\lambda,t}^1$ and glucose concentrations $G_t^1$ at wavelength $\lambda$ and time t, the corresponding feature of the validation data $Y_{\lambda,t}^2$ can be shifted with respect to the training data as shown in the FIG. 3. Portion a of FIG. 3 represents $Y_{\lambda,t}^2$ plotted with respect to $G_t^2$ are mapped with respect to the training data $Y_{\lambda,t}^1$, which results in portion b of FIG. 3. The mapped data shown in portion b is shown to give a better glucose prediction.

The below notations are used throughout the specification to represent the following:

$Y_{\lambda,t}^{ref}$ is a feature of the dominant feature set for reference vector (training data). $\lambda$ and t are used to represent the wavelength and time index respectively.

$G_t^{ref}$ is a glucose concentration of the reference vector at time t.

$Y_{\lambda,t}^{cal}$ and $G_t^{cal}$ are initial few values of the corresponding feature of the test subject and corresponding glucose concentration respectively at time t.

$Y_{\lambda,t}^{val}$ is the remaining few values of the corresponding feature of the test subject. Exclusive of $Y_{\lambda,t}^{cal}$.

$G_t^{cal}$ has 20 values, interpolated from 5 glucose measurements at interval of 5 minutes each.

Figure 4:
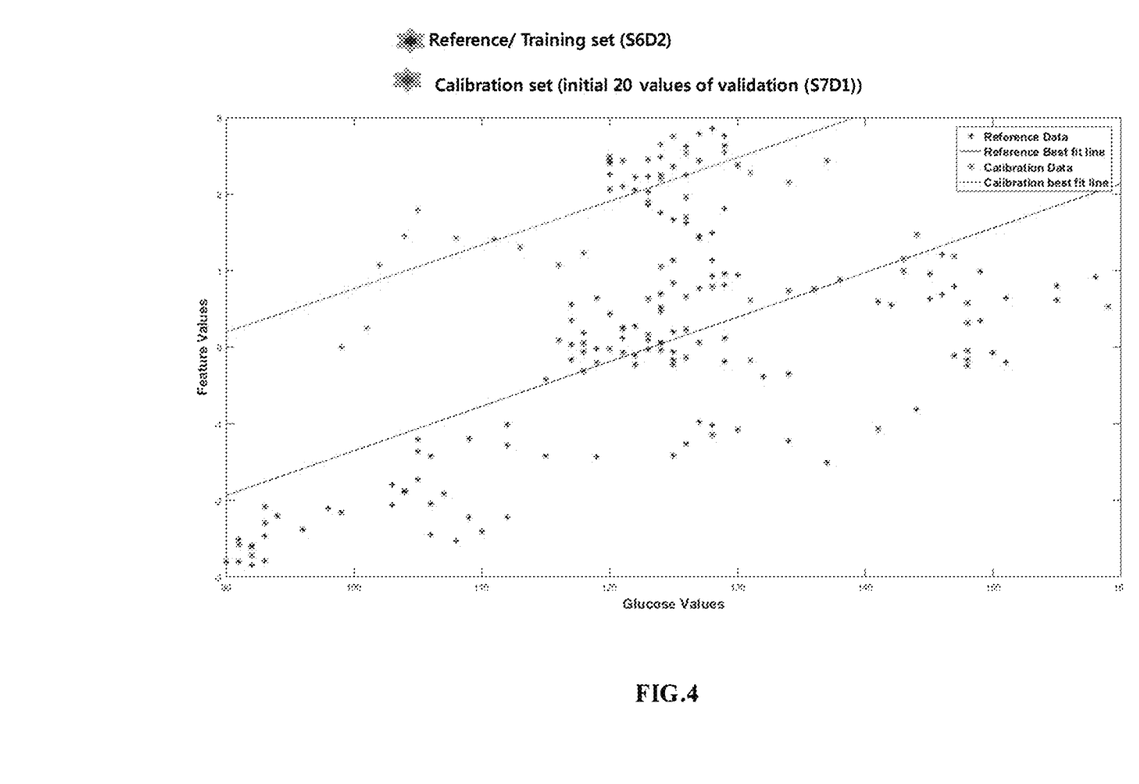
FIG. 4 is a plot representing a linear approximation relation for an 109th feature with respect to a corresponding glucose concentration of training data and calibration data, according to embodiments.

FIG. 4 is a plot representing linear approximation relation for an 109th feature with respect to a corresponding glucose concentration of training data and calibration data, according to embodiments. The embodiments herein provide a method for obtaining the liner approximation of the features with respect to the corresponding glucose concentration of the training data and the calibration data. Each pre-processed NIR feature in the dominant feature set, $Y_{\lambda,t}$ can be approximated with respect to glucose concentration as:

$$X_{\lambda,t} = m_\lambda + c_\lambda \quad (9)$$

Where $X_{\lambda,t}$ is the linear approximation for $Y_{\lambda,t}$ and $m_\lambda$ and $c_\lambda$ are slope and intercept for the $\lambda^{th}$ feature.

In embodiments, the feature of the dominant feature set for the training data and the calibration data can be linearly approximated with respect to their corresponding glucose concentrations. $m_\lambda$ may be approximately the same for both these linear approximations.

Figure 5:
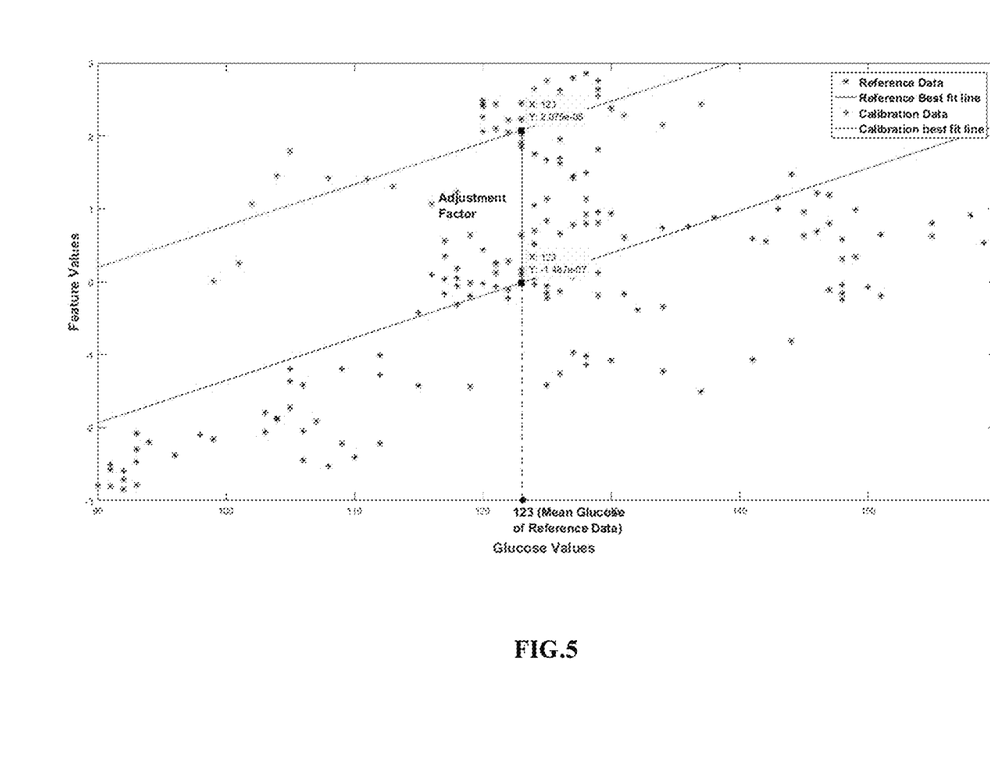
FIG. 5 is a plot representing an adjustment factor for an 109th feature in a dominant feature set of calibration data keeping training data as a reference, according to embodiments.

FIG. 5 is a plot representing an adjustment factor for an 109th feature in a dominant feature set of calibration data keeping training data as a reference, according to embodiments. The embodiments herein compute an adjustment factor for the feature of the calibration data with the training data as a reference. The adjustment factor $A_\lambda$ is the distance between NIR feature values for each feature in the dominant feature set of the training data and the calibration data at the mean glucose value of the training data using the linear approximation relation. For the mean glucose of the reference $G_{ref}^{mean}$, $A_\lambda$ is $$A_\lambda = X_{\lambda,t}^{cal} - X_{\lambda,t}^{ref} \text{ at } G = G_{mean}^{ref} \quad (10)$$

The adjustment factor $A_\lambda$ can be computed for all relevant $\lambda$ at $G_{mean}^{ref}$. The values of $A_\lambda$ can be used to map the validation data. In FIG. 5, the mean glucose reference $G_{mean}^{ref} \approx 123$ and the adjustment factor for the calibration vector for 109th feature is $$A_{109} = 2.075 \times 10^{-5} - (-1.49 \times 10^{-7}) A_{109} \approx 2.09 \times 10^{-5} \quad (11)$$

Figure 6:
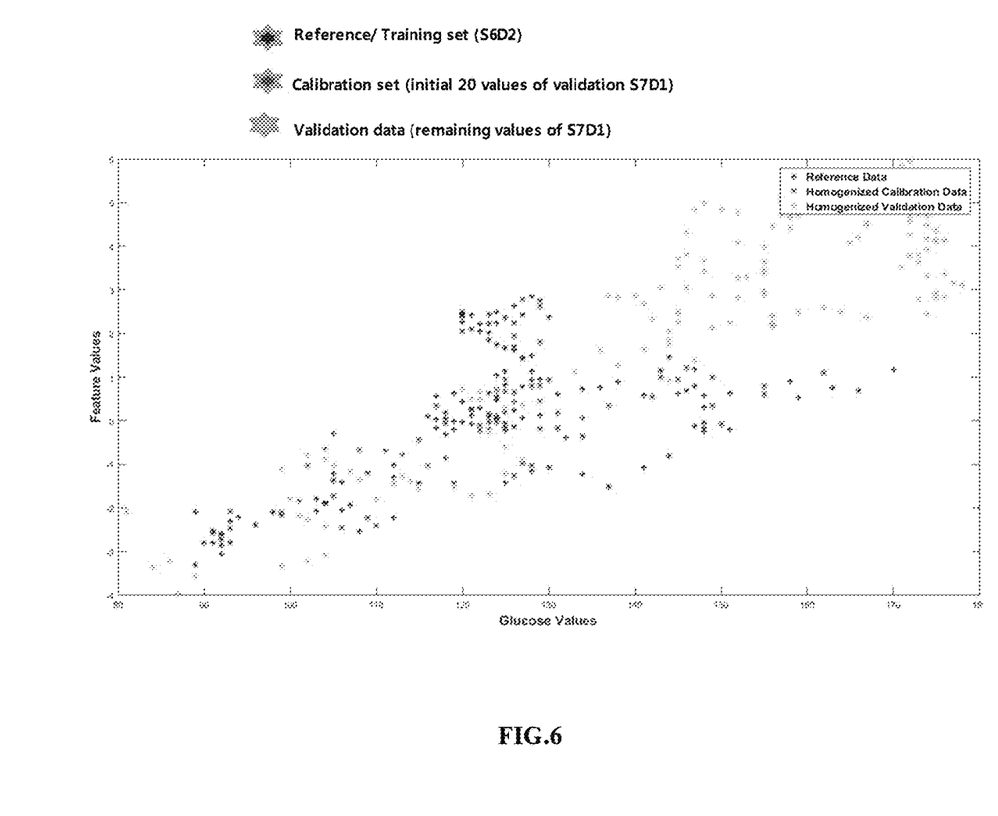
FIG. 6 is a plot representing a homogenized 109th feature of validation data and a preprocessed 109th feature of training data, according to embodiments.

FIG. 6 is a plot representing a homogenized 109th feature of validation data and a preprocessed 109th feature of training data, according to embodiments. The embodiments herein map the feature of the validation data based on the computed adjustment factor to homogenize that feature of the validation data. The adjustment factor $A_\lambda$ can be subtracted from the $Y_{\lambda,t}^{val}$ at each t.

$$Y_{\lambda,t}^{val,hom} = Y_{\lambda,t}^{val} - A_\lambda \forall t \quad (12)$$

$Y_{\lambda,t}^{ref}$ can be sent to the ensemble of regression models to train the ensemble of regression models, while $Y_{\lambda,t}^{val,hom}$ can be used for determining the blood glucose concentrations of the test subject.

Figure 7:
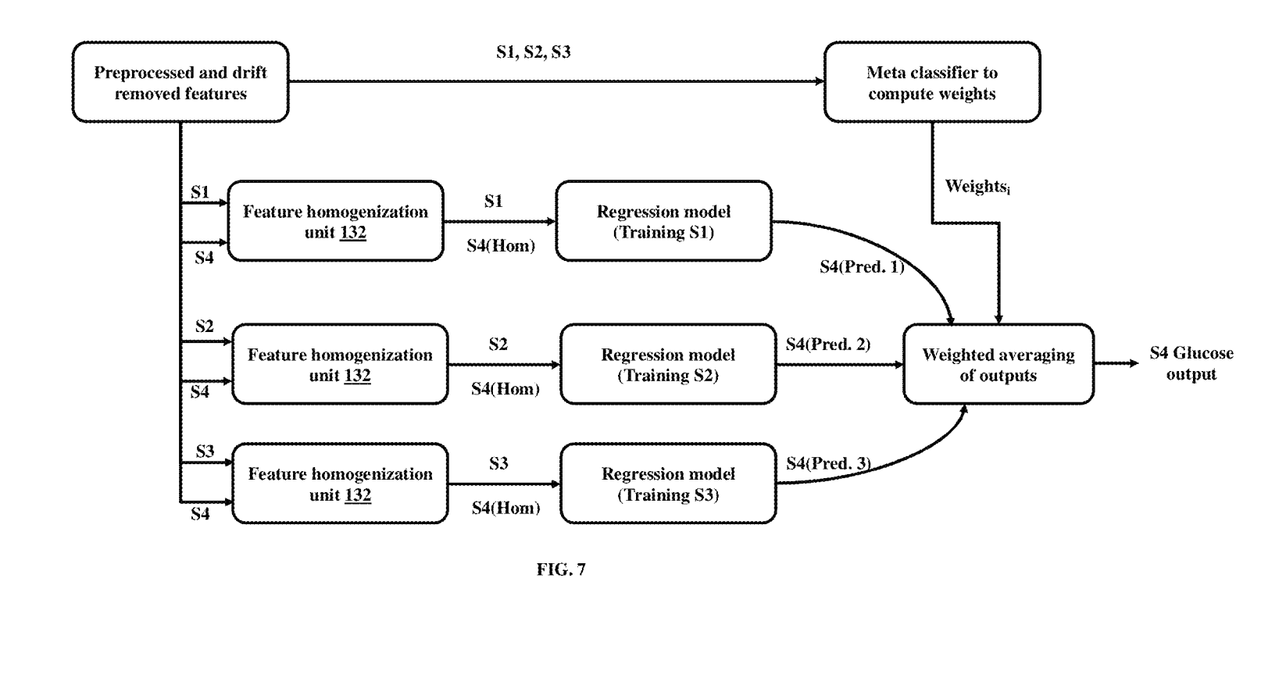
FIG. 7 is a block diagram representing an ensemble learning unit to determine the blood glucose concentration of a test subject, according to embodiments.

FIG. 7 is a block diagram representing of the ensemble learning unit 134 to generate an ensemble of regression models, use the ensemble of regression models to compute an ensemble of regression outputs, and determine a blood glucose concentration of a test subject by weighted averaging of the ensemble of regression outputs based on weights of a meta-classifier, according to embodiments.

The embodiments disclosed herein can be implemented through at least one software program running on at least one hardware device and performing network management functions to control the elements. The elements shown in FIG. 1 can be any one or any combination of a hardware device, or a combination of hardware device and software module.

The foregoing description of the specific embodiments will so fully reveal the nature of the embodiments herein that others can, by applying current knowledge, readily modify and/or adapt for various applications such specific embodiments without departing from the generic concept, and, therefore, such adaptations and modifications may and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

What is claimed is:

1. A method of determining a blood glucose concentration, using near infrared spectroscopy (NIR) spectra that is measured by an electronic device that comprises at least one processor, the method comprising:

processing, by the at least one processor, the NIR spectra and pure spectra, to obtain a preprocessed NIR spectra, wherein the preprocessed NIR spectra comprises any one or any combination of a training data of a plurality of subjects, a calibration data of a test subject and a validation data of the test subject;

extracting, by the at least one processor, a dominant feature set from the preprocessed NIR spectra, wherein the dominant feature set comprises at least one preprocessed NIR spectrum corresponding to each of the training data, the calibration data and the validation data;

obtaining, by the at least one processor, a plurality of homogenized feature sets of the validation data, wherein each of the plurality of homogenized feature sets is homogenized with respect to the extracted dominant feature set in the training data of one of the plurality of subjects and the extracted dominant feature set in the calibration data of the test subject; and determining, by the at least one processor, the blood glucose concentration of the test subject, using the training data of the plurality of subjects and the plurality of homogenized feature sets of the validation data.

2. The method of claim 1, wherein the processing of the NIR spectra and the pure spectra comprises:
  filtering, by the at least one processor, the NIR spectra to remove unwanted components in a frequency domain, from the NIR spectra;
  obtaining, by the at least one processor, orthogonal pure spectra by applying transformations on the pure spectra;
  removing, by the at least one processor, components other than glucose and water, from the filtered NIR spectra, using the orthogonal pure spectra; and
  removing, by the at least one processor, a drift from a time domain of the NIR spectra from which the components are removed.

3. The method of claim 2, wherein the filtering of the NIR spectra comprises:
  filtering, by the at least one processor, noise from the NIR spectra, using a Savitzky-Golay filter; and
  removing, by the at least one processor, a linear drift from a wavelength domain of the NIR spectra from which the noise is filtered, by differentiating the NIR spectra with respect to wavelength.

4. The method of claim 1, wherein the extracting of the dominant feature set comprises:
  computing, by the at least one processor, correlations between a glucose concentration of the training data and each of the preprocessed NIR spectra in the training data; and
  choosing, by the at least one processor, the dominant feature set, based on a maximum of the computed correlations.

5. The method of claim 1, wherein the obtaining of the plurality of homogenized feature sets comprises:
  obtaining, by the at least one processor, a singular homogenized feature set of the validation data, wherein the singular homogenized feature set is homogenized with respect to the extracted dominant feature set of the training data of the one of the plurality of subjects and the calibration data; and
  repeating, by the at least one processor, the obtaining of the singular homogenized feature set, to obtain the plurality of homogenized feature sets of the validation data.

6. The method of claim 5, wherein the obtaining of the singular homogenized feature set comprises:
  obtaining, by the at least one processor, a linear approximation relation for each of the features in the extracted dominant feature set with respect to corresponding glucose concentrations of the training data and the calibration data;
  computing, by the at least one processor, an adjustment factor for each of the features in the extracted dominant feature set for the calibration data, keeping the training data as a reference, based on the linear approximation relation; and
  mapping, by the at least one processor, each of the features in the extracted dominant feature set of the validation data by subtracting each of the features in the extracted dominant feature set of the validation data respectively from the computed adjustment factor for each of the features, to obtain the singular homogenized feature set of the validation data.

7. The method of claim 6, wherein the computing of the adjustment factor for each of the features in the extracted dominant feature set of the calibration data comprises:
  calculating, by the at least one processor, a mean glucose value for the training data;
  computing, by the at least one processor, NIR feature values for each of the features in the extracted dominant feature set of the training data and the calibration data at the calculated mean glucose value, using the linear approximation relation; and
  subtracting, by the at least one processor, the computed NIR feature values of the calibration data from the computed NIR feature values of the training data, to obtain the adjustment factor for each of the features in the extracted dominant feature set.

8. The method of claim 1, wherein the determining of the blood glucose concentration comprises:
  training, by the at least one processor, an ensemble of regression models separately with the extracted dominant feature set in the training data of the one of the plurality of subjects;
  computing, by the at least one processor, a plurality of regression outputs from the trained ensemble of regression models, taking an input for each of the ensemble of regression models respectively as the plurality of homogenized feature sets of the validation data;
  estimating, by the at least one processor, a plurality of weights of a meta-classifier for each of the ensemble of regression models, using the training data of the plurality of subjects; and
  determining, by the at least one processor, the blood glucose concentration of the test subject by weighted averaging of the computed plurality of regression outputs, based on the estimated plurality of weights of the meta-classifier.

9. The method of claim 8, wherein the estimating of the plurality of weights comprises:
  computing, by the at least one processor, a plurality of model outputs from the ensemble of regression models, taking the input for each of the ensemble of regression models as a complete set of the training data of the plurality of subjects;
  calculating, by the at least one processor, a plurality of model correlations by computing correlation between the computed plurality of model outputs and glucose concentrations of the training data of the plurality of subjects; and
  scaling, by the at least one processor, the calculated plurality of model correlations, to obtain the plurality of weights of the meta-classifier for each of the ensemble of regression models.

10. An electronic device for determining a blood glucose concentration, using near infrared spectroscopy (NIR) spectra, the electronic device comprising:
  at least one processor implementing:
    a pre-processing unit configured to process the NIR spectra and pure spectra, to obtain a preprocessed NIR spectra, wherein the preprocessed NIR spectra comprises any one or any combination of a training data of a plurality of subjects, a calibration data of a test subject and a validation data of the test subject;
    a feature set extraction unit configured to extract a dominant feature set from the preprocessed NIR spectra, wherein the dominant feature set comprises at least one preprocessed NIR spectrum corresponding to each of the training data, the calibration data and the validation data;
    a feature homogenization unit configured to obtain a plurality of homogenized feature sets of the validation data, wherein each of the plurality of homogenized feature sets is homogenized with respect to the extracted dominant feature set in the training data of one of the plurality of subjects and the extracted dominant feature set in the calibration data of the test subject; and an ensemble learning unit configured to determine the blood glucose concentration of the test subject, using the training data of the plurality of subjects and the plurality of homogenized feature sets of the validation data.

11. The electronic device of claim 10, wherein the pre-processing unit comprises:

a frequency domain filtering unit configured to filter the NIR spectra to remove unwanted components in a frequency domain;

a data whitening unit configured to obtain orthogonal pure spectra by applying transformations on the pure spectra;

an extended multiplicative scatter correction (EMSC) unit configured to remove components other than glucose and water, from the filtered NIR spectra using the orthogonal pure spectra; and a drift removal unit configured to remove a drift from a time domain of the NIR spectra from which the components are removed.

12. The electronic device of claim 11, wherein the frequency domain filtering unit is further configured to:

filter noise from the NIR spectra, using a Savitzky-Golay filter; and remove a linear drift from a wavelength domain of the NIR spectra from which the noise is filtered, by differentiating the NIR spectra with respect to wavelength.

13. The electronic device of claim 10, wherein the feature set extraction unit is further configured to:

compute correlations between a glucose concentration of the training data and each of the preprocessed NIR spectra in the training data; and choose the dominant feature set, based on a maximum of the computed correlations.

14. The electronic device of claim 10, wherein the feature homogenization unit is further configured to:

obtain a singular homogenized feature set of the validation data, wherein the singular homogenized feature set is homogenized with respect to the extracted dominant feature set of the training data of the one of the plurality of subjects and the calibration data; and repeat the obtaining the singular homogenized feature set, to obtain the plurality of homogenized feature sets of the validation data.

15. The electronic device of claim 14, wherein the feature homogenization unit is further configured to:

obtain a linear approximation relation for each of the features in the extracted dominant feature set with respect to corresponding glucose concentrations of the training data and the calibration data;

compute an adjustment factor for each of the features in the extracted dominant feature set for the calibration data, keeping the training data as a reference, based on the linear approximation relation; and map each of the features in the extracted dominant feature set of the validation data by subtracting each of the features in the extracted dominant feature set of the validation data respectively from the computed adjustment factor for each of the features, to obtain the singular homogenized feature set of the validation data.

16. The electronic device of claim 15, wherein the feature homogenization unit is further configured to:

calculate a mean glucose value for the training data;

compute NIR feature values for each of the features in the extracted dominant feature set of the training data and the calibration data at the calculated mean glucose value, using the linear approximation relation; and subtract the computed NIR feature values of the calibration data from the computed NIR feature values of the training data to, obtain the adjustment factor for each of the features in the extracted dominant feature set.

17. The electronic device of claim 10, wherein the ensemble learning unit is further configured to:

train an ensemble of regression models separately with the extracted dominant feature set in the training data of the one of the plurality of subjects;

compute a plurality of regression outputs from the trained ensemble of regression models, taking an input for each of the ensemble of regression models respectively as the plurality of homogenized feature sets of the validation data;

estimate a plurality of weights of a meta-classifier for each of the ensemble of regression models, using the training data of the plurality of subjects; and determine the blood glucose concentration of the test subject by weighted averaging of the computed plurality of regression outputs, based on the estimated plurality of weights of the meta-classifier.

18. The electronic device of claim 17, wherein the ensemble learning unit is further configured to:

compute a plurality of model outputs from the ensemble of regression models, taking the input for each of the ensemble of regression models as a complete set of the training data of the plurality of subjects;

calculate a plurality of model correlations by computing correlation between the computed plurality of model outputs and glucose concentrations of the training data of the plurality of subjects; and scale the calculated plurality of model correlations, to obtain the plurality of weights of the meta-classifier for each of the ensemble of regression models.

* * * * *